United States Patent [19]

Jones et al.

[11] Patent Number: 5,731,510
[45] Date of Patent: Mar. 24, 1998

[54] MULTI-GAS SENSOR SYSTEMS FOR AUTOMOTIVE EMISSIONS MEASUREMENT

[75] Inventors: Barbara L. Jones, Kings Lynn; Kenneth W. Peter; Thomas F. Wylie, both of Cambs, all of United Kingdom

[73] Assignee: Sun Electric U.K. Limited, King's Lynn, England

[21] Appl. No.: 667,964

[22] Filed: Jun. 18, 1996

[30] Foreign Application Priority Data

Jun. 24, 1995 [GB] United Kingdom ............... 9512929

[51] Int. Cl.$^6$ ........................................... G01M 15/00
[52] U.S. Cl. .................. 73/23.31; 73/31.06; 73/117.3
[58] Field of Search ................... 73/23.31, 23.32, 73/31.05, 31.06, 116, 117.2, 117.3, 118.1

[56] References Cited

U.S. PATENT DOCUMENTS

| | | |
|---|---|---|
| 3,696,247 | 10/1972 | McIntosh et al. . |
| 3,743,426 | 7/1973 | Steinberg . |
| 4,039,286 | 8/1977 | Keller et al. . |
| 4,347,732 | 9/1982 | Leary . |
| 4,502,939 | 3/1985 | Holfelder et al. . |
| 4,584,867 | 4/1986 | Forster . |
| 4,816,800 | 3/1989 | Onaga et al. . |
| 4,818,705 | 4/1989 | Schneider et al. . |
| 4,895,017 | 1/1990 | Pyke et al. . |
| 5,117,680 | 6/1992 | Colvin . |
| 5,138,163 | 8/1992 | Butler et al. . |
| 5,177,994 | 1/1993 | Moriizumi et al. ............ 73/23.34 |
| 5,333,487 | 8/1994 | Kimura et al. . |
| 5,343,906 | 9/1994 | Tibbals, III . |
| 5,397,442 | 3/1995 | Wachsman . |
| 5,397,541 | 3/1995 | Post . |
| 5,429,737 | 7/1995 | Pribat et al. . |
| 5,431,042 | 7/1995 | Lambert et al. ............ 73/116 |
| 5,450,749 | 9/1995 | Strom et al. ............ 73/23.32 |
| 5,507,174 | 4/1996 | Friese et al. ............ 73/23.32 |

FOREIGN PATENT DOCUMENTS

| | | |
|---|---|---|
| 089470 | 9/1983 | European Pat. Off. . |
| 2135462 | 2/1984 | United Kingdom . |
| 2182448 | 5/1987 | United Kingdom . |
| 2203249 | 2/1988 | United Kingdom . |
| 2239094 | 12/1990 | United Kingdom . |
| 2276726 | 10/1994 | United Kingdom . |
| 8501351 | 3/1985 | WIPO . |
| 9308467 | 4/1993 | WIPO . |

OTHER PUBLICATIONS

Abstract of Japanese patent document No. JP 3111749.
Abstract of Japanese patent document No. JP 2098658.
Abstract of Japanese paten document No. JP 05312709A.
"Automotive Sensors", by Westbrook et al., Institute of Physics Publishing Bristol and Philadephia (pp. 189-190).

*Primary Examiner*—George M. Dombroske
*Attorney, Agent, or Firm*—Emrich & Dithmar

[57] ABSTRACT

Gas analysis apparatus particularly applicable to the quantitative monitoring of individual gas components in automotive exhausts, and providing this function in a rapid-response and hand-held, low power consumption format, comprises an array of electrically responsive solid-state sensors to which the mixture of automotive gases to be analyzed is simultaneously fed. Monitoring the electrical response of the sensors enables a substantially instantaneous determination of the quantitative presence of individual components of the gas mixture.

6 Claims, 3 Drawing Sheets

MULTI-GAS SENSOR SYSTEMS FOR AUTOMOTIVE EMISSIONS MEASUREMENT

BACKGROUND OF THE INVENTION

1. Field of the Invention

This invention relates to a method and apparatus for gas analysis and is particularly, but not exclusively, applicable to the analysis of automotive exhaust emissions. The invention is also applicable to the analysis of exhaust emissions from other internal combustion engines. Moreover, the invention may well find application in other technical areas where there is or will be a requirement for an apparatus and method applicable to the quantitative determination of individual gases present in a mixture, and/or in which the technique is more convenient, and/or the apparatus more compact and/or less power consuming and/or able to respond more quickly to the gases sensed, than presently available equipment.

2. Description of the Prior Art

In the automotive field, long-enacted emissions control legislation, enforced by test requirements in many countries, together with more general requirements to monitor exhaust gases as an aid to automotive service and repair, has produced a requirement for an emissions analyzer in car and truck inspection and repair facilities for many years.

The primary constituents of automotive exhaust gases are oxygen, carbon dioxide, carbon monoxide, and nitrogen, the latter being from the atmosphere and passing inertly through the combustion process unchanged. Also present are smaller amounts of hydrocarbons, oxides of nitrogen ($NO_x$), oxides of sulphur ($SO_x$) and hydrogen sulphide ($H_2S$). The currently available automotive gas analyzers are able to measure the concentration of oxygen, carbon dioxide and carbon monoxide and hydrocarbons. Two techniques are currently used. These are a non-dispersive infra-red technique (NDIR) and an electrochemical cell technique. The NDIR technique is used to measure carbon dioxide, carbon monoxide and hydrocarbons, since the infra-red spectra for these oxides of carbon can be isolated and their intensity metered to obtain a quantitative determination of these gases. Also, the NDIR technique enables the spectrum of one hydrocarbon, namely n-hexane, to be measured and from it the Total Hydrocarbon Content (THC) is obtained by extrapolation from this value.

The electrochemical cell is used to analyze quantitatively the presence of oxygen, since the NDIR technique is not well applicable to that gas. A paramagnetic technique is also available for analysis of oxygen.

The above established gas sensing techniques each have significant disadvantages. For example, the NDIR unit is large and precludes incorporation into a readily portable or hand-held unit and prevents use close to the vehicle tailpipe, thus increasing the gas transit time to the apparatus and slowing response. The electrochemical cell is inherently slow to react to gas concentration changes and, on account of the consumption of the electrolyte, only has a 6 to 12-month lifetime under normal usage.

Reference is directed to the following prior proposals:
1. Automotive Sensors, MH Westbrook and JD Turner, IoP Publishing, p. 189–190.
2. Gas and Vapor Sensor; Smoke Detector, UK Patent GB 2 276 726A, filed Mar. 29, 1994.
3. New tin oxide film gas sensor . . . , Japan Patent 61 300 16.
4. Carbon diode gas detection . . . , Japan Patent 31 117 49.
5. Nitrogen dioxide gas sensor . . . , Japan Patent 20 986 58.
6. Gas sensor with highly sensitive . . . , Japan Patent 053 127 09 A.

Many single gas sensors have been developed. The zirconia oxygen sensor is in use, but the sensor is non-linear and exhibits a switching characteristic. A thick-film or cast pellet tin-oxide device has been produced for application as a carbon monoxide sensor in domestic fire alarms, but the response time is, as might be expected from the application, somewhat slow. Other tin oxide devices that incorporate a catalyst to promote selectivity have been developed for substances including hydrogen, carbon, methane, oxygen, carbon dioxide and nitrogen dioxide.

Reference is also directed to the following prior US patents:

| | |
|---|---|
| U.S. 3,696,247 | U.S. 3,743,426 |
| U.S. 4,502,939 | U.S. 4,816,800 |
| U.S. 4,818,705 | U.S. 5,117,680 |
| U.S. 5,138,163 | U.S. 5,333,487 |
| U.S. 5,343,906 | U.S. 5,397,442 |
| U.S. 5,397,541 | |

Of the above patents the US '705 specification discloses an automotive exhaust gas analyzer in which a light beam is absorbable by the exhaust gas and a plurality of measurements cells are traversed by radiation of the light beam while the exhaust gas flows through the cells. However, neither this specification nor any of the others discloses the combination of an array of electrically responsive solid state gas sensor elements which are simultaneously subjected to an input gas mixture to enable an analytical procedure to be instantaneously effected in accordance with requirements of the automotive field, as disclosed in the embodiments described below.

SUMMARY OF THE INVENTION

We have identified a requirement for a more unified approach to automotive exhaust analysis and related applications as discussed above, in which a single technique for analysis of multiple gas components is applicable, thereby permitting simplification in the process of supplying the gas mixture to be tested to the apparatus and in performing the tests themselves, and, indeed, in analyzing and presenting the resulting data.

An object of the present invention is to provide a method and apparatus applicable to the quantitative analysis of multi-gas mixtures and capable of providing such apparatus in relatively compact and/or relatively portable and/or relatively rapidly responding form, and/or such apparatus making significantly reduced power requirements as compared with existing apparatus.

According to the invention there is provided gas analysis apparatus and a corresponding method together with gas sensor apparatus as defined in the accompanying claims.

The invention also provides such method and apparatus not limited by all such features of any of the said claims, but comprising a novel combination of features leading to a technical advance as disclosed herein.

In an embodiment of the invention, gas analysis apparatus comprises multiple gas sensor elements with associated gas input and output means. The multiple gas sensor elements comprise an array of individually electrically responsive solid state sensor elements. These sensor elements are mounted in relation to the gas input and output means so that an input flow of said gas mixture is passed substantially simultaneously over all the gas sensor elements. By virtue of this arrangement of sensor elements, and the associated feature of presentation of same to the gas flow, the advantage is provided of convenience and compact format, the solid state sensor elements are able to respond rapidly and in a quantitative fashion. In this way the requirements for portability and instantaneous convenient usage in relation to particular gas mixtures and emissions is obtained.

In the described embodiments, a first embodiment comprises interconnected discrete sensor units to which a flow of exhaust gas is directed via piping. A pump and mass flow meter and associated control valves are provided to enable sampling to be undertaken on a repetitive constant volume basis.

In a second embodiment, the sensor units are incorporated in a unitary monolithic structure in which the gas flow paths and control thereof are provided by micro-machined channels. In this way a smaller overall size is achieved and appreciable cost benefits.

In the embodiments, at least one sensor is provided for each one of the individual gases in the mixture to be detected. Additional sensor elements, per gas, are provided where there is a requirement for coloration or compensation for a reduced susceptibility to technical faults.

The solid state sensor elements may comprise:

(a) a polymer-coated quartz crystal microbalance (QCM), (b) a metal-oxide-coated QCM, (c) a polymeric or metal-oxide resistor or capacitor, (d) Chemfet (a Field Effect Transistor (FET) with modification, usually to the gate, to make the drain current dependent on gas concentration), (e) SAW (a Surface Acoustic Wave delay—line oscillator that is modified to make phase-velocity and oscillator frequency dependent on gas concentration), and (f) resonator structures and fluorescent optrodes.

The sensor elements are incorporated into the structure so as to permit easy access for servicing.

Also in the embodiments, the signal outputs from the sensor array are electronically processed to access the test gas concentration information. This is achieved by means of a look-up table or by an algorithm-controlled calculator function, or a more sophisticated deconvolution or neural network technique.

These and other features of the invention are attained by providing gas analysis apparatus for the analysis of a gas mixture comprising multiple gas components, the apparatus comprising:

(a) an array of individual electrically responsive solid state sensor elements each responsive to one of said gas components of said mixture, each of said sensor elements being adapted to respond to its one of said gas components by an electrically detectable change in an electrical or other physical parameter of said element enabling a quantitative determination of the presence of said component;

(b) electrical output means coupled to said array to enable the display of quantitative data derived from said sensor elements relating to said multiple gas components; and c) gas input and output means receiving said gas mixture and mounted in relation to said array and then discharged from the apparatus so that an input flow of said gas mixture is passed substantially simultaneously over all of said sensor elements.

BRIEF DESCRIPTION OF THE DRAWINGS

Embodiments of the invention will now be described by way of example with reference to the accompanying drawings in which.

DESCRIPTION OF THE PREFERRED EMBODIMENT

Figure 1:
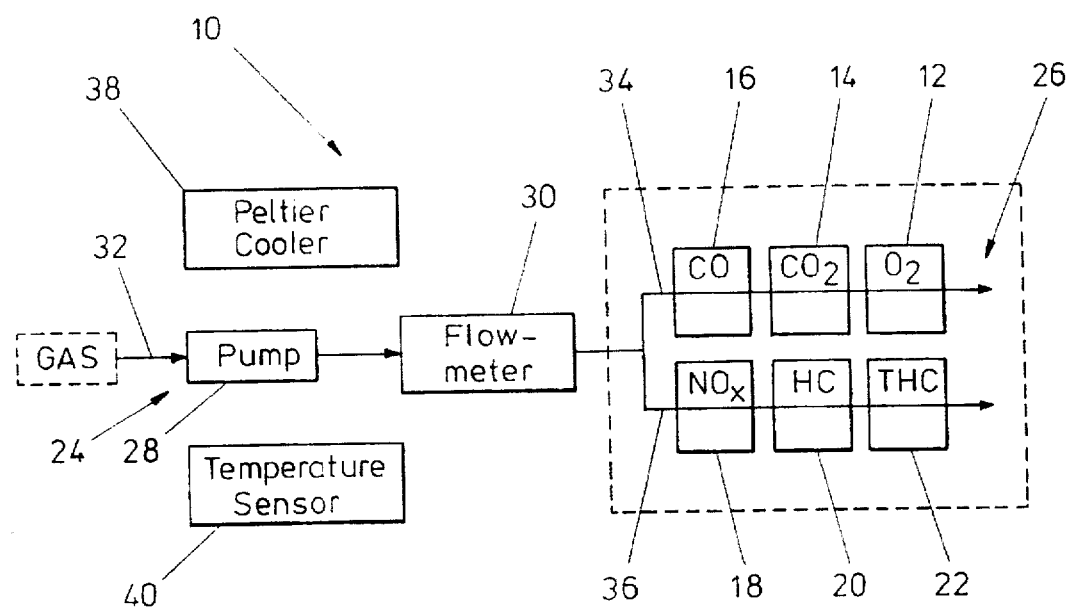
FIG. 1 shows in block diagram form gas analysis apparatus comprising an array of discrete sensors interconnected by conduits.

As shown in the drawings, the gas analysis apparatus 10 of FIG. 1 comprises multiple gas sensor elements 12, 14, 16, 18, 20 and 22 to sense and quantitatively determine the indicated individual gas components.

As described below, the sensor elements 12 to 22 are provided with electrical output means to enable the display of quantitative data derived from the sensor elements and relating to the individual multiple gas components.

Gas input and output means 24 and 26 are provided to receive the gas mixture and to present same to the gas sensor elements and to permit the gas mixture to be discharged from the apparatus.

As is clear from FIG. 1, the sensor elements 12 to 22 are in the form of an array of individual electrically responsive sensor elements. Each one is in solid state form, being a substrate of quartz crystal and having a gas-responsive coating thereon.

A pump 28 and an associated gas flow meter 30 are provided to receive the gas mixture to be analyzed (for example from an automotive exhaust) at 32. The output from flow meter 30 is delivered via conduits 34, 36 substantially simultaneously to the sensor elements 12 to 22 by grouping these as shown. In a modification (not shown) the sensors are arranged to be provided with the sample gas from flow meter 30 through conduits of substantially equal length for achieving simultaneous sampling.

A Peltier effect cooling assembly 38 is provided under the control of a temperature sensor 40 and is brought into effect where regulation of the apparatus temperature is required, for example when sampling relatively hot gases from an automotive tail pipe.

Figure 2:
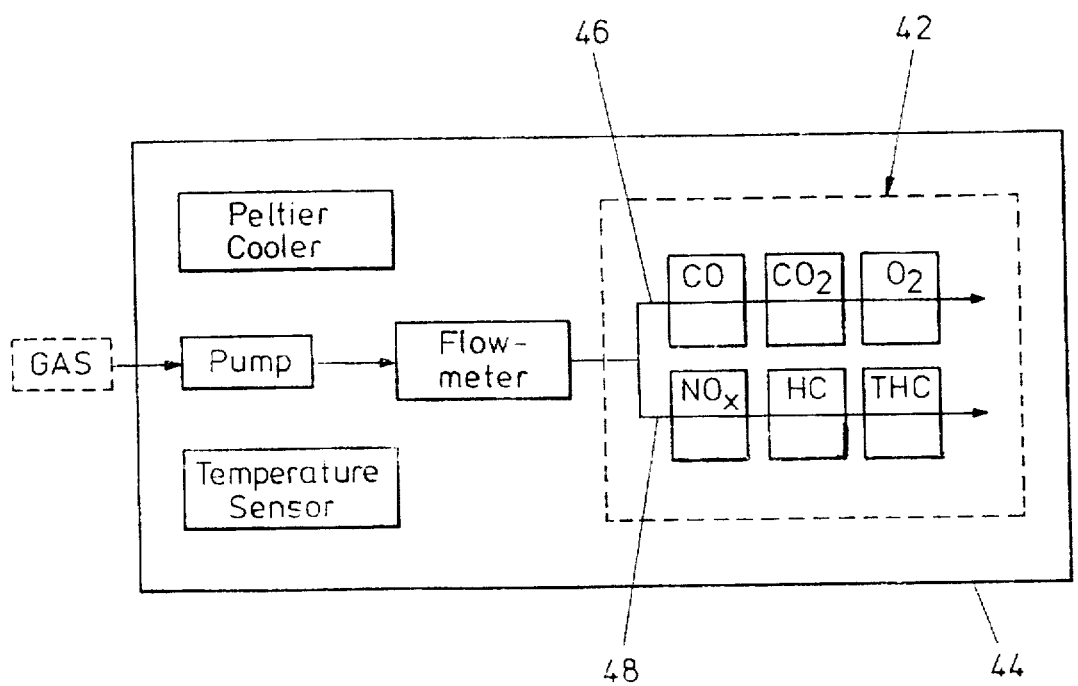
FIG. 2 shows, in similar diagrammatic form, apparatus comprising a corresponding sensor array provided in a monolithic micromachined assembly.

In the embodiment of FIG. 2, the general structure and arrangement is similar to that of FIG. 1, but in this case the assembly 42 of sensor elements forms part of a monolithic molded structure 44 patterned in an appropriate material, e.g., silicon, metal, plastic, high temperature ceramic or a polymer, such as polysiloxane. In the monolithic structure, micro gas flow channels are produced by micromachining and microengineering techniques. Such is indicated at 46 and 48 in FIG. 2. The showing of these channels in similar form to FIG. 1 is to be interpreted accordingly in view of the above description.

As indicated in FIGS. 1 and 2, the sensors 12 to 22 are constructed to sense and measure concentrations of, respectively, oxygen, carbon dioxide, carbon monoxide, oxides of nitrogen, hydrocarbons (n-hexane) and total hydrocarbon content. Each sensor comprises a quartz crystal microbalance substrate carrying a gas-sensitive coating comprising a metal oxide or a polymer, as discussed in more detail below. In the case of the oxygen sensor, there is employed a fluorescence optrode operating on the basis of the measurement of the decrease in fluorescence intensity of a fluorophore dye when it is quenched by molecular (triplet) oxygen. The optrode may, for example, be based on measurement of the fluorescence lifetime determined by the phase lag between a fluorescence signal and an internal reference rectangular voltage. See "Phase Fluorometric Sterilizable Optical Oxygen Sensor", S B Bambot et al, Biotechnology and Bioengineering, Vol. 43 pp. 1139–1145 (1994).

Figure 3:
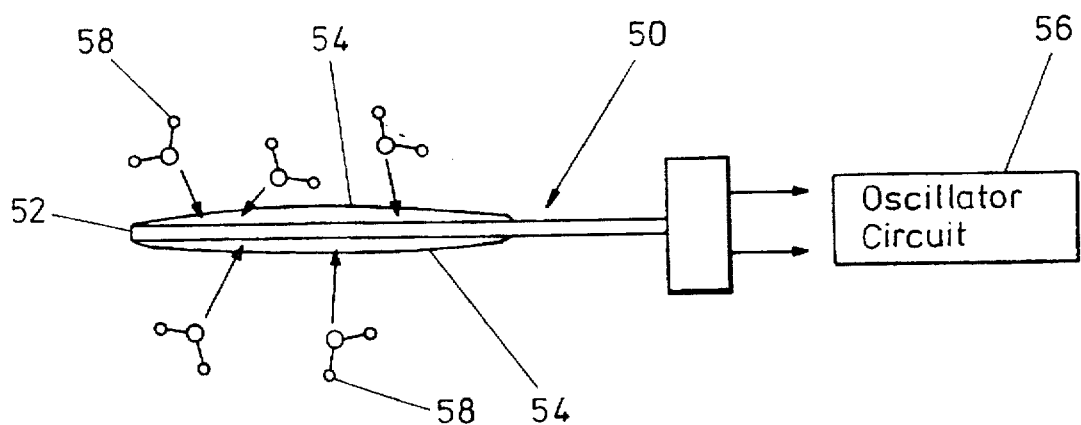
FIGS. 3 and 4 are diagrammatic representations of the function or operation of individual sensor elements.

Turning to FIG. 3, there is shown a sensor element 50 comprising a piezoelectric crystal 52, for example having a 10 MHz fundamental frequency having gold plated electrodes and coated with a thin film coating 54 of target gas-absorbing polymer. The polymer comprises polysiloxane and is deposited to a thickness of 50 nm (nanometers) to 10 micrometers by spraying or spin-coating or metal organic chemical vapor deposition. The polymer selectively absorbs the target gas by one or more of the contemplated mechanisms described below.

With respect to the response time of the sensor elements, it is expected that a response time of approximately 1 second should be sufficiently rapid for many purposes and is apparently achievable subject to some variations due to differing gas diffusion rates, which leads to some degree of selectivity in relation to particular gases in a given gas mixture.

Macrocylic complexes of the transition metals, e.g., cobalt may be incorporated into the polymer structure as chemo-receptor sites, to bind chemically with the particular gas to be sampled. Further compounds may be included, either to repel from the receptor sites undesired components in a gas cocktail, e.g., a hydrophilic structure, or to create structural "lock and key" access to the receptor sites.

Sensor element 50 forms part of an oscillator circuit 56 providing a frequency output. As the coated element 50 is immersed in the gas mixture under test, the coating 54 selectively absorbs the target gas molecules, thus increasing the coating mass. This mass loading has the effect of causing a measurable negative shift in the oscillation frequency of the crystal. This frequency shift will be of the order of hundreds of hertz.

In FIG. 3, the molecules of gas are indicated at 58 in diagrammatic fashion.

Figure 4:
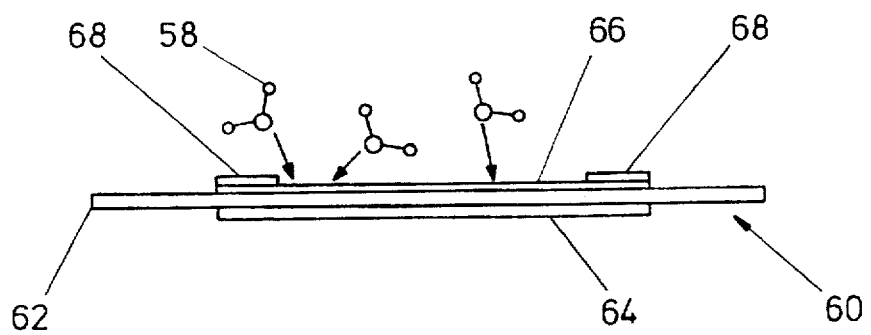

Turning now to FIG. 4, the sensor element 60 is in the form of a plate 62 of alumina (or silicon or glass or diamond or the like) and has a heater element 64, for use where required, provided at its underside by a screen printing or deposition step. The gas- selective film 66 is provided at a depth of 50 nanometers to 10 micrometers, and is deposited on the substrate by screening printing or CVD (Chemical Vapor Deposition) and has metal contacts 68 at either end of the film provided by screen printing, evaporation or sputtering.

The gas-selectivity of the metal-oxide film is provided by a catalyst combined with the metal oxide, either as a layer above or below the metal oxide film, or mixed therewith. This catalyst is either a transition metal, such as platinum or palladium or vanadium, or a compound of an element of groups IIA IIIA IIIB IVA or IVB of the periodic table. Selectivity is additionally promoted by maintaining the oxide at a predetermined temperature by means of the heater element 64 or by the composition of the oxide, e.g., the thickness or crystal structure of same. A sensitivity, for example, of 25 ohms per part per million of target gas, and a response time of less than 1 second, may be achieved by mixing an organic binding agent to the metal oxide, which after formation of the active layer is driven off during the thermal curing process, thus increasing the porosity of the film.

Electrical contacts 68 provide the data output. Gas molecules are indicated at 58, as in FIG. 3.

In use, the sensor elements 50 and 60 show a characteristic change in conductance due to exposure to the selected gas, which is proportional to the target gas concentration. The resistance of the sensor element forms part of a bridge circuit to permit compensation for temperature or humidity.

Figure 5:
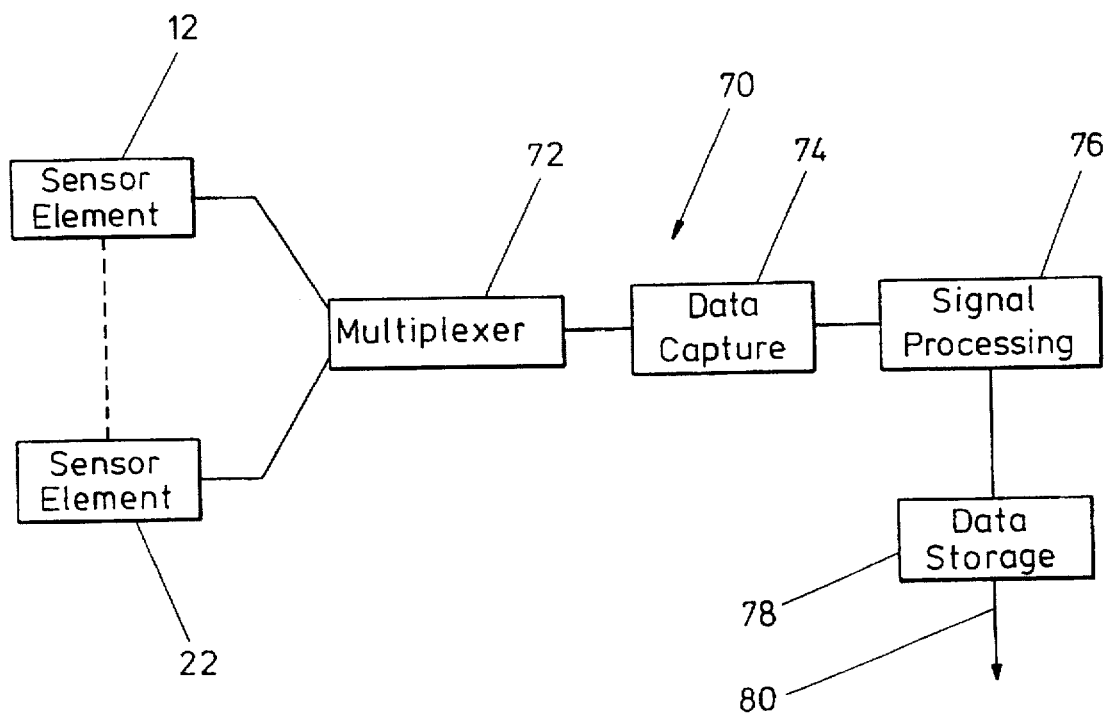
FIG. 5 shows a block diagram illustrating the sequence of functional operations in the overall apparatus employing sensor elements accessed serially by a multiplexer.

FIG. 5 shows the overall circuit diagram in which the output from the sensor elements 12 to 22 (or 50 or 60) is coupled to a data-acquisition and processing circuit 70. The multiple sensor elements 12 to 22 are accessed serially by multiplexer 72 and the thus-sampled data is captured at 74, processed at 76 and stored at 78. The stored data is available for output at 80, including display on a convenient liquid crystal monitor for example.

The signal processing circuit may operate on one of the sensor element values using a look-up table or algorithm. Alternatively, a series of values, which may be either a series of successive values from one sensor element, or values from several different sensor elements, or a combination of both, are processed, e.g., by a neural net.

Figure 6:
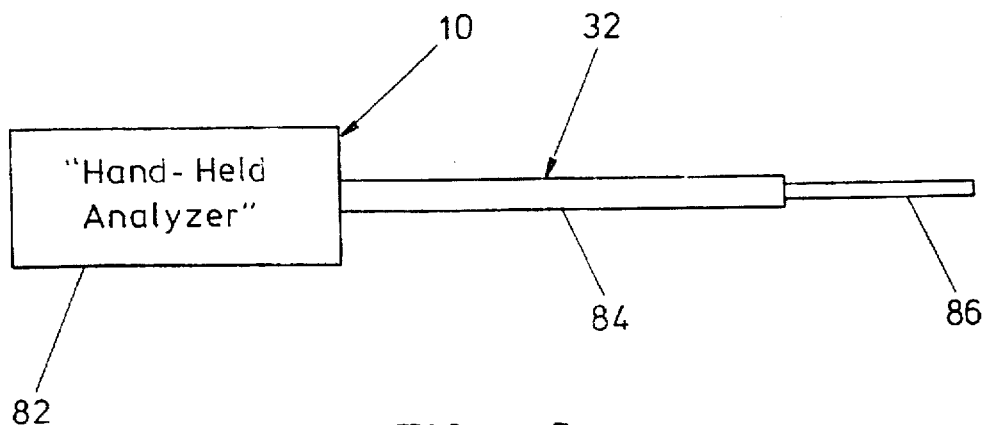
FIG. 6 shows in simple diagram form a practical embodiment of the apparatus of FIGS. 1 to 5 including the analysis apparatus and a gas-sampling tube/probe assembly.

As shown in FIG. 6, the practical embodiment of the apparatus of FIGS. 1 to 5 provides essentially the gas analysis apparatus 10 in the form of a hand-held analyzer 82, and analyzer 82 is provided with automotive exhaust input gas at 32 by means of a sample tube 84 and a tail-pipe probe 86.

Analyzer 82 is constructed in relatively light weight and hand-holdable form incorporating the systems of apparatus 10 described above.

Sample tube 84 is fabricated in a material which is flexible and gas and liquid-impermeable, and is connected to the tail-pipe probe 86.

Probe 86 is insertable into the tail-pipe of a vehicle under test to receive a continuous flow of exhaust gas at a temperature between 20 degrees Celsius and 150 degrees Celsius. This gas supply is drawn into the apparatus by pump 24 (see FIG. 1) and proceeds via sample tube 84.

Probe 86 is of a length and design such as to prevent siphoning of atmospheric air into the system from the end of the tail-pipe, thus preventing dilution of the sample exhaust gas and preventing consequential erroneous measurement.

Pump 24 creates a vacuum within the body of analyzer 82 to draw sampled gas to the array of sensor elements 12 to 22. The pump, preferably of a diaphragm type, has a gas flow capacity of less than 18 liters per minute.

In use, the gas to be sampled enters the analysis chamber containing the array of discrete interconnected solid-state gas sensors 12 to 22 and the gas flow is such that the sample is brought into contact with all the sensor elements substantially simultaneously. After analysis the spent gas is vented from the analyzer body to atmosphere.

Signal processing and analysis proceeds as described above, including conversion from analogue to digital format, processing, storage and display of the concentrations of the gases of interest, as likewise described above.

We claim:

1. Automotive emissions measurement apparatus for the analysis of a gas mixture comprising multiple gas components from an automotive internal combustion engine, the apparatus comprising:

(a) an array of individual electrically responsive non-electrolytic solid state sensor elements each responsive to contact with one of said gas components of said mixture, each of said sensor elements being adapted to respond to its one of said gas components by an electrically detectable change in an gas components by an electrically detectable change in an electrical or other physical parameter of said element enabling a quantitative determination of the presence of said component each of said sensor elements including a substrate selected from the group comprising quartz crystal and alumina and silica, said substrate having a gas-responsive coating thereon;

(b) electrical output means coupled to said array to enable the display of quantitative data derived from said sensor elements relating to said multiple gas components; and (c) gas input and output means mounted in relation to said array for receiving said gas mixture and discharging it from the apparatus so that an input flow of said gas mixture is passed substantially simultaneously over all of said sensor elements in direct contact with each.

2. Apparatus according to claim 1, wherein said coating includes a polymer or a metal oxide or a metal or a fluorophore.

3. Apparatus according to claim 1, wherein said sensor elements are adapted to respond to their respective gas components by a change in conductance or resistance.

4. Apparatus according to claim 1, and further comprising at least one Peltier effect cooling element adapted to effect cooling of said apparatus and/or the gas mixture supplied to said sensor elements.

5. Apparatus according to claim 1, and further comprising a gas flow meter located upstream of said sensor elements and adapted to monitor the flow rate of gas supplied thereto, whereby constant volume sampling may be achieved.

6. A method for the analysis of a gas mixture including multiple gas components from an automotive internal combustion engine, the method comprising the steps of: providing multiple non-electrolytic gas sensor elements respectively for said multiple gas components, each of said sensor elements including a substrate selected from the group comprising quartz crystal and alumina and silica, said substrate having a gas-responsive coating thereon, feeding said gas mixture substantially simultaneously into contact with all of said sensor elements, and determining the electrical response of individual ones of said sensor elements to their corresponding gas components to obtain quantitative data relating to said multiple gas components.

* * * * *